(12) United States Patent
Sambanthamurthi et al.

(10) Patent No.: US 10,183,054 B2
(45) Date of Patent: Jan. 22, 2019

(54) COMPOSITIONS COMPRISING EXTRACTS OR MATERIALS DERIVED FROM PALM OIL VEGETATION LIQUOR FOR INHIBITION OF VISION LOSS DUE TO ANGIOGENESIS AND METHOD OF PREPARATION THERE

(71) Applicant: Malaysian Palm Oil Board, Kajang (MY)

(72) Inventors: Ravigadevi Sambanthamurthi, Darul Ehsan (MY); Yew Ai Tan, Darul Ehsan (MY); Ali Hafezi-Moghadam, Jamaica Plain, MA (US)

(73) Assignee: MALAYSIAN PALM OIL BOARD, Kajang, Selangor (MY)

( * ) Notice: Subject to any disclaimer, the term of this patent is extended or adjusted under 35 U.S.C. 154(b) by 24 days.

(21) Appl. No.: 15/488,874

(22) Filed: Apr. 17, 2017

(65) Prior Publication Data

US 2017/0274035 A1    Sep. 28, 2017

Related U.S. Application Data

(63) Continuation of application No. 14/452,405, filed on Aug. 5, 2014, now abandoned, which is a continuation of application No. 14/118,209, filed as application No. PCT/MY2012/000102 on May 18, 2012, now abandoned.

(30) Foreign Application Priority Data

May 18, 2011 (MY) .......................... PI 2011002220

(51) Int. Cl.
*A61K 36/889* (2006.01)
*A23L 2/02* (2006.01)
*A23L 33/105* (2016.01)

(52) U.S. Cl.
CPC .............. *A61K 36/889* (2013.01); *A23L 2/02* (2013.01); *A23L 33/105* (2016.08)

(58) Field of Classification Search
CPC ..................................................... A61K 36/889
USPC .......................................... 424/727, 776, 777
See application file for complete search history.

(56) References Cited

U.S. PATENT DOCUMENTS

| 2003/0031740 | A1 | 2/2003 | Sambanthamurthi et al. |
| 2007/0243211 | A1 | 10/2007 | Jaffe |
| 2009/0226547 | A1* | 9/2009 | Gilbard ................ A61K 31/353 424/729 |
| 2009/0252817 | A1 | 10/2009 | Hayes et al. |

OTHER PUBLICATIONS

Wattanapenpaiboon et al. Phytonutrient deficiency: the place of palm fruit, "North & West African Foods and Health", Feb. 8, 2003, Marrakech, Morocco). (Year: 2003).*
Nakagawa et al., "In Vivo Angiogenesis Is Suppressed by Unsaturated Vitamin E, Tocotrienol," J. Nutr., (2007), 137(8):1938-1943.
PCT International Search Report dated Feb. 1, 2013 in PCT Patent Application No. PCT /MY2012/000102.
Wattanapenpaiboon et al. "Phytonutrient deficiency: the place of palm fruit", Asia Pacific J /clinical Nutrition, 2003:12(3) pp. 363-368.
"Age-related macular degeneration", The Lancet, vol. 372, Issue 9652, Nov. 22-28, 2008, pp. 1835-1845.

* cited by examiner

*Primary Examiner* — Christopher R Tate
*Assistant Examiner* — Deborah A Davis
(74) *Attorney, Agent, or Firm* — Melissa M. Hayworth

(57) ABSTRACT

The present invention relates generally to a composition comprising palm fruit juice for use in a method of preventing and inhibiting vision loss due to angiogenesis related diseases. The composition of the present invention aids to decrease in CNV size using confocal microscopy, in addition to reduction in macrophage infiltration using immune staining; decrease in VEGF-A-induced angiogenesis using established cornea pocket assay, inhibition of IKB-D phosphorylation in laser treated choroidal tissues and reduction in macrophage recruitment to CNV lesions.

15 Claims, 3 Drawing Sheets

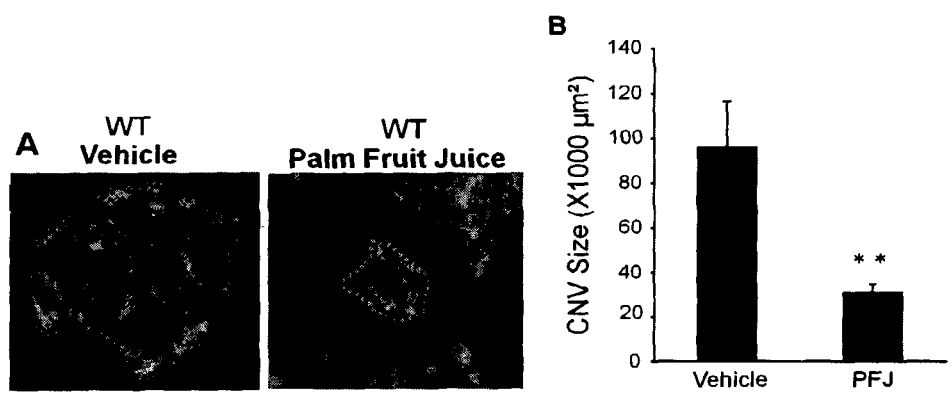
FIG 1 (a) and (b)
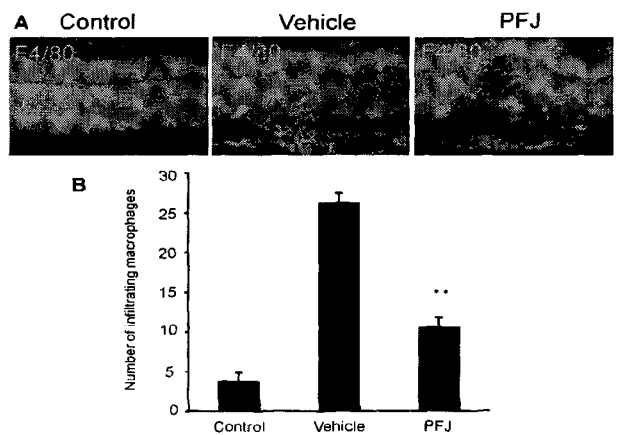
FIG 2 (a) and (b)

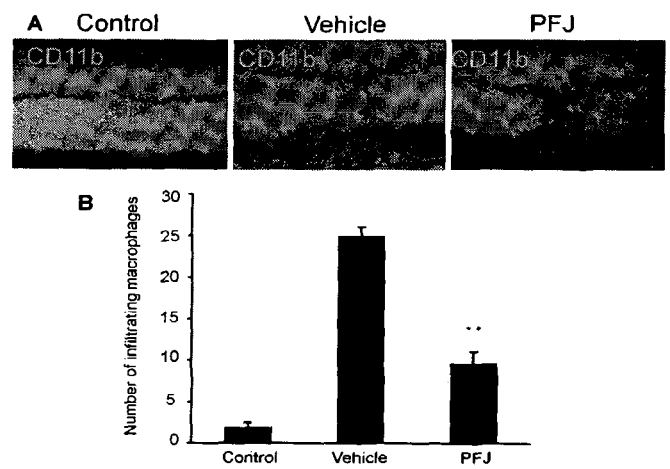
FIG 3 (a) and (b)
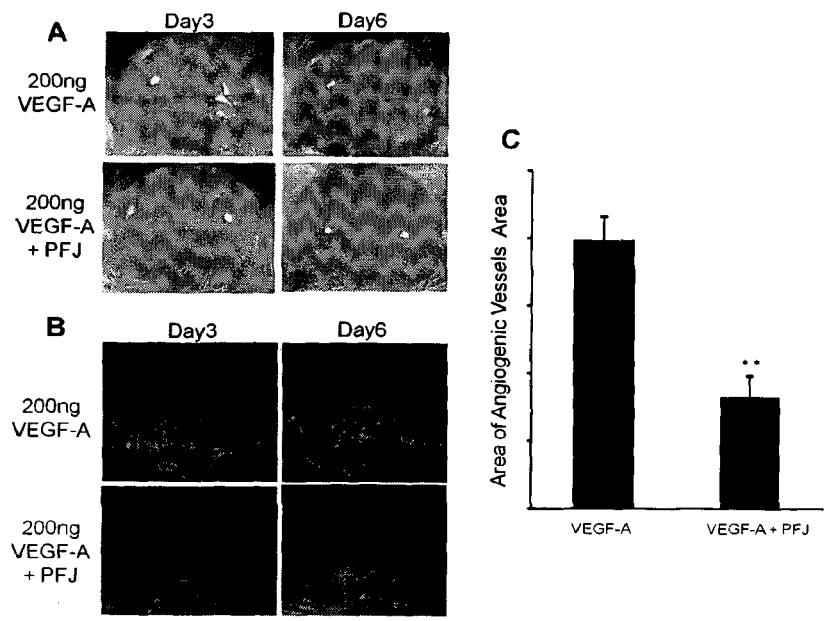
FIG 4 (a), (b) and (c)

COMPOSITIONS COMPRISING EXTRACTS OR MATERIALS DERIVED FROM PALM OIL VEGETATION LIQUOR FOR INHIBITION OF VISION LOSS DUE TO ANGIOGENESIS AND METHOD OF PREPARATION THERE

CROSS-REFERENCE TO RELATED APPLICATIONS

This application is a continuation of U.S. application Ser. No. 14/452,405 filed Aug. 5, 2014, which is a continuation of U.S. application Ser. No. 14/118,209 filed Nov. 15, 2013, now abandoned, which is a U.S. National Stage Application under 35 U.S.C. § 371 of International Application No. PCT/MY2012/000102 filed May 18, 2012, which claims priority to Malaysian Application No. PI 2011002220 filed May 18, 2011, each of which is incorporated herein by reference in its entirety.

FIELD OF INVENTION

The present invention relates generally to compositions based on oil palm plant and more particularly to compositions comprising materials obtained from palm oil vegetation liquor for the treatment and prevention of ocular inflammatory and vascular diseases, such as Age-Related Macular Degeneration (AMD).

BACKGROUND

Reference to any prior art in this specification is not, and should not be taken as, an acknowledgement or any form of suggestion that this prior art forms part of the common general knowledge in Malaysia or any other countries.

Angiogenesis relates to the formation or sprouting of new blood vessels from preexisting vessels. Under normal circumstances, angiogenesis is observed as the formation of blood vessels during, but not limiting to, wound healing and embryonal development. For the past few years, great efforts have been expended by researchers to understanding the regulation of angiogenesis, identifying pathways to angiogenesis and much has been written about the mechanisms as well as its pathologic and physiologic conditions. There are three major processes or stages involved in the formation of blood vessels; whereby the first stage is angiogenic activation of endothelial cells and degradation of basement membrane, the second stage is endothelial proliferation and migration, and the third stage is new vessel formation.

Stages of maturation and stabilization of the newly formed blood vessels occur by means of recruitment of pericytes which may involve angiogenic factors such as vascular endothelial growth factor (VEGF). Accordingly, vascular endothelial growth factor (VEGF) plays a major role in all these three main stages. It facilitates in inducing angiogenic activated state of endothelial cells for the blood vessel, proliferation and migration of stimulus from the preexisting blood vessel and expression of integrins in new vessel formation.

One of the major causes of human blindness or adult vision loss is age-related maculopathy, especially in industrialized countries. Generally, such cause is associated to interference of normal physiological process of angiogenesis as described earlier, particularly due to local expansion of blood vessels, or uncontrolled angiogenesis.

An example of a leading cause of adult vision loss is age-related macular degeneration (AMD). Recent studies have demonstrated that AMD is caused by an assortment of clinically ocular findings that leads to vision impairment and blindness. Generally, AMD occurs in two forms, dry and wet. In wet AMD, choroidal vessels pathologically grow through the retinal pigmented epithelial (RPE) cell layer into the subretinal space, a process known as choroidal neovascularization (CNV). According to scientific reports, CNV and ensuing leakage damage to the RPE and retinal cells would lead to permanent vision loss.

Because VEGF is an important biomarker in angiogenesis (Zahir K Otrock, 2010) in many cases, VEGF has been identified as the key molecule responsible for the growth and leakiness of CNV, and the primary regulatory factor of neovascularization of angiogenic diseases. It can be concluded that VEGF, is one of the most significant factors affecting endothelial cell (EC) proliferation, among others, its motility and vascular permeability.

Macrophages are a major source of VEGF and tumor necrosis factor (TNF)-□, thereby it is implicated in the pathogenesis of AMD due to their spatiotemporal distribution in the proximity of the CNV lesions particularly in experimental models and humans.

In US 2007203211 A1, there is disclosed a drug for use in preventing or treating angiogenic eye diseases, in which the method involves administering to a mammal in need thereof pharmaceutically effective amount of angiotensin II receptor antagonist. It is further disclosed that angiotensin II receptor antagonist is highly effective in the prevention or treatment of intraocular angiogenic diseases such as proliferative retinopathy or retinal vein occlusion. There is no explicit disclosure on using plant based materials as VEGF inhibitors.

A great majority of treatments and medications are chemical based or surgical based treatments which may not be favorable for patients at advanced ages. Further, it has been shown that treatment for AMD is effective for only a small proportion of patients, particularly patients who have well-defined choroidal neovascular membrane (CNVM) (Bressler et al, 2004).

Therefore, there is a need to identify a solution and effective treatment for ocular angiogenesis and thus inhibits human blindness derived from highly abundant sources, such as plant based materials.

It is primary object of the present invention to provide a composition and method thereof for use in the prevention and inhibition of vision loss due to angiogenesis associated diseases.

Still other objects of the present invention will become readily apparent to those skilled in the art from the following detailed description.

SUMMARY OF INVENTION

The present invention relates to the prevention and inhibition of vision loss due to ocular angiogenesis by a composition comprising palm fruit juice.

In accordance with the present invention there is provided a composition comprising materials obtained from palm oil vegetation liquor, used for prevention and inhibition of vision loss due to ocular angiogenesis diseases.

In accordance with the present invention, the composition may be used in a method for inhibiting vision loss due to angiogenesis mediated or associated diseases, for instance but not limiting to ocular neovascularization, macular degeneration or any diseases where inhibition of angiogenesis is required.

In an additional aspect, the composition of the present invention may be used in a method for prevention of vision loss due to diseases associated with angiogenesis and VEGF receptor phosphorylation.

BRIEF DESCRIPTION OF DRAWINGS

Some figures contain color representations or entities in order to elucidate the results of experiments for the purpose of the present invention.

FIGS. 1(a) and (b) shows the effect of palm fruit juice (PFJ) of the present invention on CNV formation;

FIGS. 2(a) and (b) shows the macrophage infiltration in CNV in accordance with a preferred method of the present invention;

FIGS. 3(a) and (b) shows the leucocyte activation in experimental AMD;

FIGS. 4(a), (b) and (c) shows tissues areas of angiogenesis in corneas;

DETAILED DESCRIPTION

Figure 5:
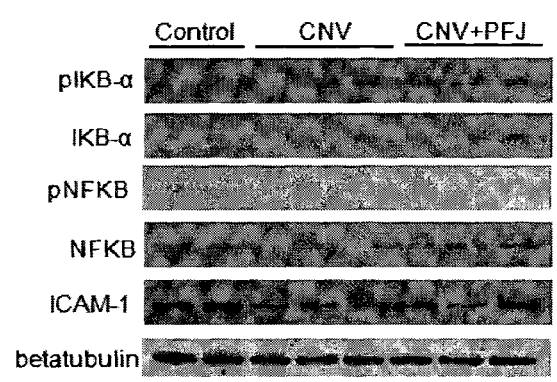
FIG. 5 shows the western blot of pIKβ-☐, IKB-☐, pNFKB and NFKB in experimental AMD with and without palm fruit juice treatment.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Embodiments of the invention are described by way of illustration. As will be realized, the invention is capable of other and different embodiments and its several details are capable modifications in various respects, all without departing from the spirit and/the scope of the present invention.

In accordance with the present invention, the composition comprises materials or extracts obtained from palm oil vegetation liquors, whereby said vegetation liquors maybe obtainable either directly from plants or as waste streams or aqueous streams in the processing of plant material. The vegetation liquors may be obtained based on wastes from any processing stages of oil palm at a palm oil mill.

Further in accordance with the present invention, the materials or extracts obtained from palm oil vegetation liquor of palm oil milling process are water soluble.

The materials or extracts obtained from palm oil vegetation liquor of the present invention contains phenolics.

The present invention provides a composition and method thereof for use in the treatment of ocular angiogenesis, and in particular age-related macular degeneration (AMD), whereby said composition is based on oil palm plants of the species *Elaeis*.

The present invention thereby introduces a novel composition and a novel method of medical treatment.

A particular aspect of the present invention contemplates a method for preparing a medicament based on a composition comprising materials obtained from vegetation liquors, for instance, palm fruit juice, in the treatment of an ocular angiogenesis.

Yet another aspect of the present invention provides a composition comprising extracts, more particularly palm fruit juice obtained from vegetation liquor for the treatment of an ocular angiogenesis, and more particularly, a macular degeneration associated diseases, such as, but not limiting to age-related macular degeneration (AMD).

Throughout the specification, the term "*Elaeis* sp" which may be used includes *Elaeis guineensis* and *Elaeis oleifera*.

As a preliminary example, it is described below the effects of extracts derived from oil palm vegetation liquor against CNV; more particularly said extract is palm fruit juice.

Materials and Methods

In order to examine the effects of PFJ against vision loss, several experiments will be elucidated as examples were carried out and the results obtained will be described herein.

The palm fruit juice (PFJ) may be obtained by conventional means, from pure palm nut. The juice for use in the purpose of the present invention may contain other components however not to disrupt the nutritional content of fruit juice.

According to the present invention, the Palm Fruit Juice (PFJ) provides significant decrease in VEGF-A-induced angiogenesis. Such effect can be examined with a standard method of corneal micropocket assay as provided in EXAMPLE 1 below.

Example 1

Corneal Micropocket Assay

Balb/C mice were anesthetized with an intraperitoneal injection of ketamine (100 mg/kg) and xylazine (10 mg/kg). Hydron pellets (0.3 μl) containing 25, 100, 200, 400 or 1600 ng human VEGF-A (293-VE; R&D Systems), 200 ng mouse VEGF-A (493-MV; R&D systems), were prepared and implanted into the corneas. Pellets were positioned in around 1.0±0.2 mm distance to the corneal limbus. After implantation, bacitracin ophthalmic ointment (E. Fougera & Co) was applied to each eye to prevent an infection. On the indicated days after the implantation, digital images of the corneal vessels were obtained and recorded using OpenLab software version 2.2.5 (Improvision Inc) with standardized illumination and contrast.

Example 2

Quantification of Angiogenesis in Whole-Mount

The mice were perfused with rhodamin-ConA and the eyes were taken out, radial cuts were then made in the peripheral cornea to allow flat mounting on a glass slide using a mounting medium (TA-030-FM, Mountant Permaflour; Lab Vision Corporation). The flat-mounted tissues were examined by fluorescence microscopy and recorded using OpenLab software version 2.2.5 (Improvision Inc) with standardized illumination and contrast. The results obtained were recorded.

Example 3

Laser-Induced CNV

To induce CNV, C57BL/6 mice were anesthetized and pupils were dilated with 5% phenylephrine and 0.8% tropicamide. Using a 532-nm laser (Oculight GLx, Iridex, Mountain View, Calif.), a slit-lamp delivery system, and a cover glass as a contact lens, four spots (100 mW, 50 μm, 100 ms) were placed in each eye. The lesions were located at 3, 6, 9 and 12 o'clock meridians centered on the optic nerve head and located ~2 to 3 disk diameter from the optic nerve head. Development of a bubble under laser confirmed the rupture of the Bruch's membrane. Eyes showing haemorrhage were excluded from experiments. The results obtained for this step were recorded.

In accordance with another preferred embodiment of the present invention, PFJ decreases the CNV size, whereby an analysis to evaluate this effect is shown in EXAMPLE 4 below:

Example 4

Evaluation of CNV

Seven days after laser injury, the size of the CNV lesions was measured in choroidal flat mounts. Briefly, mice were anesthetized and perfused through the left ventricle with PBS, followed by 5 ml of fluorescein-labeled dextran (5 mg/ml, fluorescein isothiocyanate-dextran; Sigma Aldrich) in 1% gelatin. Anterior segment and retina were removed from the eyecup. The remaining RPE-choroid-sclera complex was flat mounted after relaxing radial incisions using Mounting Medium (TA-030-FM, Mountant Permafluor; Lab Vision Corporation) and coverslips. Micrographs of the choroidal complex were taken using a Confocal Microscope (Leica, Wetzlar, Germany). The magnitude of the CNV lesions was determined by measuring the hyperfluorescent area using Openlab Software (Improvision, Boston, Mass.). The results obtained for this step were accordingly recorded.

According to another preferred embodiment of the present invention, the PFJ decreases macrophage infiltration, whereby a standard method can be used to examine such effect, as elucidated in EXAMPLE 5 below.

Example 5

Immune Histochemistry

On day 3 after laser injury 10 μm frozen sections of the posterior segment were prepared. The sections were incubated with a mouse anti-F4/80 mAb (10 μg/ml), and subsequently with the secondary antibody. Photomicrographs of the CNV lesions were taken and the number of F4/80 positive macrophages was counted.

Example 6

Western Blot

To obtain tissues, animals were perfused with PBS and eyes were enucleated immediately after perfusion. Choroid was microsurgically isolated and placed into 100 μl of lysis buffer (mammalian cell lysis kit MCL 1, Sigma Chemical Co, St. Louis, Mo.), supplemented with protease and phosphatase inhibitors (Sigma), and sonicated. The lysate was centrifuged (12000 rpm, 15 min, 4° C.) and the supernatant was collected. Each sample containing equal amount of total protein, quantified by protein assay (Bio-Rad Laboratories, Inc, CA) was separated by SDS-PAGE (sodium dodecyl sulfate-polyacrylamide gel electrophoresis), and electroblotted to PVDF (polyvinylidene fluoride) membranes (Invitrogen, Carlsbad, Calif.). To block the nonspecific binding the membranes were washed with 5% skim milk and subsequently incubated with a rabbit polyclonal antibody against (1 μg/ml, Santa Cruz Biotechnology, Santa Cruz, Calif.) or a mAb against β-tubulin (1.5 μg/ml; Abcam, Cambridge, Mass.) at 4° C. overnight, followed by incubation with a horseradish peroxidase-conjugated donkey or sheep antibody against rabbit or mouse IgG (1:2000; GE Healthcare UK limited Buckinghamshire, UK). The signals were visualized with chemiluminescence (ECL kit; GE Healthcare UK limited, Buckinghamshire, UK) according to the manufacturer's protocol.

Statistics

All values are expressed as mean±SEM. Data were analyzed by t-test and differences between the experimental groups were considered statistically significant or highly significant, when the probability value, p, was <0.05 or <0.01, respectively.

Results

Results obtained from each experiment were suitably recorded and analyzed via conventional means.

I. Reduction of CNV Size in Experimental AMD Using PFJ

To examine the potential of PFJ in reducing CNV, mice were fed PFJ for two weeks prior to laser injury. On day seven after CNV induction, CNV Volume was measured using confocal microscopy.

FIGS. 1(a) and (b) shows the representative micrographs of CNV lesions in choroidal flat mounts from animals treated with vehicle or PFJ orally. Red dashed lines show the amount of CNV lesions filled with FITC-dextran. FIG. 1(b) shows the quantitative analysis of CNV volume. As evident in FIG. 1, it is observed that the CNV volume was reduced significantly compared to vehicle-fed controls.

II. Reduction of Microphage Infiltration Experimental AMD Using PFJ

To investigate the effect of PFJ on macrophage infiltration in AMD, immune staining for the macrophage-specific marker, F4/80, and quantified the number of F4/80 positive cells in CNV lesion were performed. It is found and shown in FIGS. 2(a) and (b) that macrophages were recruited to the CNV lesion one week after laser injury. In comparison, the number of accumulated macrophages at this time point was significantly reduced.

FIG. 2(a) shows fluorescent micrograph of a laser induced CNV lesion, vehicle and treated with PFJ, immunostained with F4/80. The green shade shows the amount of macrophage infiltration with CNV lesion. FIG. 2(b) shows the quantitative analysis of macrophage infiltration. Bars show the average of macrophages number, n=3, P□0.05.

In order to investigate macrophage activation in the CNV lesion, immune staining was performed for CD11b, a leukocyte activation marker, and quantified the number of CD11b positive cells in CNV lesion. One week after laser injury it is observed that a significant number of activated immune cells accumulated in CNV lesions of vehicle fed animals. In contrast, it is observed that the number of activated leukocytes was significantly reduced in PFJ-fed animals. The results obtained based on this experiment were tabled and plotted as FIGS. 3(a) and (b).

FIG. 4(a) shows the tissue areas of angiogenesis in corneas based on a preferred embodiment of the present invention. Digital images of the corneal vessels on $3^{rd}$ and $6^{th}$ day of VEGF-A implantation. Images in FIG. 4(b) shows the fluorescence microscopy of flat mounted cornea tissues, whereby on the $6^{th}$ day the mice were perfused with rhodamin-ConA.

FIG. 4(c) shows a plotted graph based on the quantitative analysis of the angiogenesis area. Based on this experiment, it is shown that the average of area (n=3), P□0.05.

III. Suppression of Pro-Inflammatory Signaling Experimental AMD Using PFJ

Investigation on the effect of PFJ on angiogenesis on a molecular level was performed based on implanted hVEGF-A (200 ng) in corneas of mice that were fed vehicle or PFJ. To examine, whether PFJ reduces angiogenesis, on $3^{rd}$ and $6^{th}$ day after the implantation, digital images of the corneal vessels were obtained and subsequently quantified. Results based on this experiment are shown in FIG. 5, wherein a western blot of pIKB-☐, IKB-☐, pNFKB and NFKB in experimental AMD with and without Palm Fruit Juice (PFJ) treatment, three days after laser injury, while the control are unlasered eyes.

From the above, as it is widely known that immune cells and more particularly macrophages play a significant role in AMD pathology, disruption of monocyte recruitment and infiltration into ocular tissues may aid in preventing disease development and progression.

According to the present invention, it is shown in the experimental results that subjects fed or treated with Palm Fruit Juice (PFJ), exhibited:
  a) Significant decrease in CNV size using confocal microscopy, in addition to reduction in macrophage infiltration using immune staining;
  b) Significant decrease in VEGF-A-induced angiogenesis using established cornea pocket assay;
  c) Inhibition of IKB-☐ phosphorylation in laser treated choroidal tissues with PFJ;
  d) Reduction in macrophage recruitment to CNV lesions.

As briefly mentioned in earlier sections, in accordance with the present invention, the composition may be used in a method, for inhibiting vision loss due to angiogenesis mediated or associated diseases, for instance but not limiting to ocular neovascularization, macular degeneration or any diseases where inhibition of angiogenesis is required.

In another aspect of the present invention, the composition may be used for providing protective effect in diabetic retinopathy or damages to the eye's retina, various types of glaucoma which may lead to blindness or eyes disorders and corneal transplants.

Further, the composition of the present invention may be used in a method for prevention of vision loss due to diseases associated with angiogenesis and VEGF receptor phosphorylation.

Generally, the composition comprising palm fruit juice (PFJ) may be prepared in various suitable forms for direct or oral administration for the purpose of preventing adult vision loss.

According to the present invention, the PFJ of the present invention may be used to make supplements, or contained in drinks, edible products, tonics, health supplements, cosmetics. It is clear that PFJ may be prepared in concentrated form or extract.

Compositions suitable for oral administration may be presented in discrete units, such as capsules, sachets, lozenges, or tablets, each containing a pre-determined amount of the extract: as a powder or granules; as a solution or a suspension in an aqueous or non-aqueous liquid. Such compositions may be prepared by any suitable method of pharmacy which includes the step of bringing into association the extract of the present invention and one or more suitable carriers (which may contain one or more accessory ingredients as noted below). In general, the compositions of the invention are prepared by uniformly and intimately admixing the extract or any form of the palm fruit juice (PFJ) with a liquid or finely divided solid carrier, or both, and then, if necessary, shaping the resulting mixture. For example, a tablet may be prepared by compressing or moulding a powder or granules containing the extract or any form of the palm fruit juice (PFJ), optionally with one or more accessory ingredients.

Compressed tablets may be prepared by compressing in a suitable machine, the extracts in the form of a powder or granules, optionally mixed with a binder, lubricant, inert diluents, and/or surface active/dispersing agent(s). Moulded tablets may be made by moulding, in a suitable machine, the powdered compound moistened with an inert liquid binder.

Compositions may be prepared in a manner, and in a form/amount as is conveniently practiced.

As mentioned, the compositions of the invention may also be administered to a human in a dietary supplement form. Dietary supplements incorporating the active composition can be prepared by adding the composition to a food in the process of preparing the food. Any food may be used including, but not limited thereto, meats such as ground meats, emulsified meats and marinated meats; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen deserts, and non dairy frozen deserts; yoghurts; soaps; puddings; bakery products; salad dressings; and dips and spreads such as mayonnaise, butter, butter substitute, and other fat containing spreads. The composition is added to the food in an amount selected to deliver a desired dose of the composition to the consumer of the food.

Further, an effective amount of the compositions of the present invention is administered to a human subject. The actual dosage levels will depend upon a number of factors, such as specific mode of administration, the condition being treated, the condition of the patient and the judgement of the health care giver.

The composition comprising any form of the present invention may be prepared for use in a pharmaceutically effective or nutraceutically effective amount, solely on its own or in combination with other agents or compounds deemed appropriate by a person skilled in the art.

It is noted that the term 'pharmaceutically effective' and 'nutraceutically effective' amount includes a quantification that is acceptable for improving or prevention of vision loss, due to macular degeneration associated diseases.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for treating vision loss due to an angiogenesis associated disease and VEGF receptor phosphorylation, said method comprising administering to a patient in need thereof an effective amount of an extract derived from palm oil vegetation liquor, wherein the extract is palm fruit juice.

2. The method of claim 1, wherein the angiogenesis related disease is associated with macular degeneration.

3. The method of claim 1, wherein the disease is age-related macular degeneration (AMD).

4. The method of claim 1, wherein the effective amount of the extract provides protective effects against glaucoma, diseases associated with glaucoma, or corneal transplants.

5. The method of claim 1, wherein the effective amount of the extract provides protective effects against diabetic retinopathy and diseases associated thereto.

6. The method of claim 1 wherein the extract is a water soluble component derived from palm oil vegetation liquor.

7. The method of claim 1 wherein the extract contains phenolics.

8. The method of claim 1, wherein the angiogenesis associated disease is an ocular angiogenesis associated disease.

9. The method of claim 3, wherein the effective amount of the extract reduces the size of choroidal neovascularization (CNV) lesions in AMD.

10. The method of claim 3, wherein the effective amount of the extract reduces macrophage infiltration in AMD.

11. The method of claim 1, wherein the effective amount of the extract suppresses VEGF-A-induced angiogenesis.

12. The method of claim 3, wherein the effective amount of the extract suppresses pro-inflammatory signaling in AMD.

13. The method of claim 1, wherein the effective amount of the extract inhibits IKB-α phosphorylation in choroidal tissues.

14. The method of claim 3, wherein the effective amount of the extract reduces macrophage recruitment to CNV lesions in AMD.

15. The method of claim 1, wherein the effective amount of the extract inhibits vision loss due to ocular neovascularization.

* * * * *